(12) United States Patent
Wik

(10) Patent No.: US 10,918,817 B2
(45) Date of Patent: Feb. 16, 2021

(54) VENTILATION

(71) Applicant: Oslo Universitetssykehus HF, Oslo (NO)

(72) Inventor: Lars Wik, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 1163 days.

(21) Appl. No.: 14/906,997

(22) PCT Filed: Jul. 21, 2014

(86) PCT No.: PCT/EP2014/065592
§ 371 (c)(1),
(2) Date: Jan. 22, 2016

(87) PCT Pub. No.: WO2015/011077
PCT Pub. Date: Jan. 29, 2015

(65) Prior Publication Data
US 2016/0158472 A1     Jun. 9, 2016

(30) Foreign Application Priority Data
Jul. 24, 2013   (GB) .................. 1313170.1

(51) Int. Cl.
*A61M 16/00* (2006.01)
*A61H 31/00* (2006.01)

(52) U.S. Cl.
CPC ....... *A61M 16/0003* (2014.02); *A61H 31/005* (2013.01); *A61M 16/0051* (2013.01);
(Continued)

(58) Field of Classification Search
CPC .......... A61M 16/0003; A61M 16/0051; A61M 2205/50; A61M 2230/005;
(Continued)

(56) References Cited

U.S. PATENT DOCUMENTS 3,425,409 A     2/1969  Isaacson et al.
4,397,306 A *   8/1983  Weisfeldt ............. A61H 9/0078
                                                       601/41

(Continued)

FOREIGN PATENT DOCUMENTS

GB       2446826 A        8/2008
WO    2010/059049 A2      5/2010
WO    2010/148412 A1     12/2010

OTHER PUBLICATIONS

Stecher et al., Transthoracic impedance used to evaluate performance of cardiopulmonary resuscitation during out of hospital cardiac arrest, Dec. 2008, Resuscitation, vol. 79, Issue 3, pp. 432-437 (Year: 2008).*

(Continued)

*Primary Examiner* — Kendra D Carter
*Assistant Examiner* — Elliot S Ruddie
(74) *Attorney, Agent, or Firm* — Miller Nash Graham and Dunn

(57) ABSTRACT

There is provided a method of controlling a mechanical ventilator. The method may include the steps of receiving a measurement of transthoracic impedance of a patient obtained during chest compressions, determining a timing for a mechanical ventilator to provide a ventilation based on the measurement of transthoracic impedance, and sending a signal to control the mechanical ventilator based on the determined timing. There is also provided an apparatus for performing the method.

21 Claims, 1 Drawing Sheet

(52) U.S. Cl.
CPC .......... *A61H 31/006* (2013.01); *A61H 31/007* (2013.01); *A61H 2230/65* (2013.01); *A61H 2230/655* (2013.01); *A61M 2205/50* (2013.01); *A61M 2230/005* (2013.01); *A61M 2230/65* (2013.01)

(58) Field of Classification Search
CPC .......... A61M 2230/65; A61M 16/0048; A61H 2031/003; A61H 31/004; A61H 31/005; A61H 31/006; A61H 31/007; A61H 2230/65; A61H 2230/655; A61H 31/00–003
See application file for complete search history.

(56) References Cited

U.S. PATENT DOCUMENTS

| | | | |
|---|---|---|---|
| 4,840,167 A | | 6/1989 | Olsson et al. |
| 6,155,257 A | * | 12/2000 | Lurie .................. A61H 31/005 128/204.18 |
| 2004/0230113 A1 | * | 11/2004 | Bolam ................. A61M 16/12 600/410 |
| 2009/0020127 A1 | * | 1/2009 | Boone ............... A61M 16/0051 128/207.14 |
| 2010/0106208 A1 | | 4/2010 | Freeman |
| 2010/0114220 A1 | * | 5/2010 | Paradis ................ A61H 31/005 607/6 |
| 2010/0312153 A1 | | 12/2010 | McIntyre et al. |
| 2011/0224587 A1 | * | 9/2011 | Freeman ............... A61H 31/004 601/43 |
| 2012/0216804 A1 | | 8/2012 | Lurie et al. |
| 2013/0023781 A1 | * | 1/2013 | Freeman .............. A61B 5/0535 600/529 |
| 2014/0150781 A1 | * | 6/2014 | Di Capua ................ A61N 1/39 128/202.16 |

OTHER PUBLICATIONS

PCT International Search Report and Written Opinion for PCT Application No. PCT/EP2014/065592 dated Oct. 10, 2014 (14 pages).

GB Search Report for GB Application No. 1313170.1 dated Jan. 20, 2014 (3 pages).

* cited by examiner

VENTILATION

TECHNICAL FIELD

The invention relates to a method of controlling a ventilator and an apparatus for carrying out the method.

BACKGROUND OF THE INVENTION

It is known to provide manual ventilations using a self inflating bag to a patient during cardiopulmonary resuscitation (CPR). This is achieved by a person manually providing ventilation whilst chest compressions are performed on a patient.

SUMMARY OF THE INVENTION

In a first aspect, the present invention provides a method of controlling a mechanical ventilator, the method comprising: receiving a measurement of transthoracic impedance of a patient obtained during chest compressions; determining a timing for a mechanical ventilator to provide a ventilation based on the measurement of transthoracic impedance; and sending a signal to control the mechanical ventilator based on the determined timing.

When CPR is being performed on a patient it is important that ventilations are performed at the correct time. If the ventilations are not correctly synchronised with the chest compressions being performed, intrathoracic damage may be caused and/or the heart may be prevented from properly refilling. These problems may be avoided by having a person administer manual ventilations so that they can determine the most appropriate time to provide a ventilation. However this requires an additional person during CPR and is vulnerable to human error.

Thus the present invention may provide a method of controlling a mechanical or automatic ventilator to provide a ventilation at the correct time during CPR. This is achieved by monitoring the transthoracic impedance (TTI) of the patient during chest compressions and controlling the mechanical ventilator based on this monitored parameter. This means that ventilation during chest compressions can be provided reliably and at the correct time relative to the chest compressions.

The method may control the mechanical ventilator to provide a ventilation between two chest compressions. This may be achieved by causing the ventilation to be performed immediately after one of the chest compressions is performed and by providing the ventilation over a time period which is less than the time (e.g. average time) between two chest compressions.

As a result, transthoracic impedance fluctuations generated by chest compressions may be used to synchronize mechanical ventilations between two chest compressions.

The ventilator may only provide a ventilation when a signal is received to perform a ventilation. In other words, the method may be such that each time it is desired to provide a ventilation to the patient, a signal is sent to the ventilator.

The ventilator may not provide ventilations at a certain or predetermined rate. Instead the ventilator may provide ventilations at a time which is dependent on the time over which a number of chest compressions are performed. The transthoracic impedance measurements may be used to determine timing for a mechanical ventilator to be triggered to provide a ventilation. Thus, the signal to control the mechanical ventilator may be a trigger signal.

The determined timing may be so as to provide a certain (e.g. predetermined) ratio of compressions to ventilations. This may be when the patient being ventilated has an unsecured airway.

The determined timing may therefore be so as to cause a ventilation to be provided between two chest compressions and/or so as to cause a certain ratio of chest compressions: ventilations.

The method may include inputting or setting a ratio of compressions to ventilations which controls the ratio of compressions to ventilations.

The ratio of compressions to ventilations may be set according to medical guidelines. For example, the guidelines set out in Anonymous. 2010 *American Heart Association Guidelines for Cardiopulmonary Resuscitation and Emergency Cardiovascular Care Circulation* 210;122:S298-S946 or Anonymous. *European Resuscitation Council Guidelines for Resuscitation* 2010. *Resuscitation* 2010;81:1219-1433.

As a result, the ratio of compressions to ventilations may change over time. The ratio of chest compressions to ventilations may be different between infants, children and adults.

Currently the recommended ratio for adults is 30:2 and hence when an adult is being ventilated the determined timing may be such as to cause the ratio of chest compressions to ventilations to be 30:2. However the recommended ratio has been known to be 15:2. In other words the guidelines can change and thus the desired ratio of chest compressions to ventilations may vary over the years. Thus the determined timing may be so as to cause the ratio of chest compressions: ventilations to be according to current medical guidelines.

The ratio of chest compressions: ventilations may be 30:2 or 15:2 or between 15:2 and 30:2, such as 10:1. The ratio may depend on the recommended medical guidelines at the time the method is performed.

When the patient has an unsecured airway it may be necessary for chest compressions to be paused whilst the ventilation is provided. This is to minimise the risk that a ventilation is provided whilst a chest compression is performed.

If there is a pause, it is preferable for the pause to not be more than one or two seconds during continuous chest compressions, in accordance with the Guidelines for the compression: ventilation ratios.

Thus, the method may comprise providing an indication signal which is for indicating that the chest compressions should be paused so a ventilation can be provided safely. For example, the indication signal could be activated after a certain number (such as 15, 5, 4 or 3) of chest compressions has been performed.

The indication signal may be an audible signal such as a beep, and/or a visual signal, such as a light flash.

The present invention is based on impedance measurement of the thoracic cavity. This measurement is performed from the outside of the thorax. Impedance measurement involves the use of at least two electrodes which receive an approximately constant direct (or alternating) current. From this, a measurement of the direct (or alternating) voltage between the electrodes can be obtained so that calculation of the ratio voltage/current (impedance) can be performed. In an embodiment the supplied current is an alternating current with a frequency range of between 10 and 100 kHz, e.g. 80 kHz.

The principle behind the invention is that the transthoracic impedance of inflated lungs is different from that of deflated (or empty) lungs. This is due to the increase in the amount of insulator (air) between the electrodes when the lungs are inflated. The invention makes use of this change in impedance during chest compressions to monitor the chest compressions.

The term "impedance" refers generally to a complex value comprising a resistive and an inductive/capacitive part, but it is possible to implement the invention by measuring only the resistive/capacitive and/or inductive part of the impedance. The measurements can be performed by means of AC or DC voltage/current. In the DC case, only the resistive part of the impedance will be measured. However, use of DC for measurement will be inappropriate because the body tissue is capacitive. A DC measurement will then just reflect the resistance of the skin layer. Because of this, in a preferred embodiment of the invention AC voltage/current is used. Measurement of voltage/current/conductance may be employed in an equivalent way for determining the thoracic impedance.

The method may comprise obtaining a measurement of the transthoracic impedance of a patient during chest compressions.

The chest compressions may be being performed manually or performed by a machine.

The measurement may be achieved by using a TTI measurement device. The TTI measurement device may comprise at least two electrodes. To obtain a TTI measurement, the electrodes may be placed on a patient's thorax, and then a current sent through the electrodes. The voltage drop across the electrodes may then be monitored to obtain an impedance value which is a transthoracic impedance value. This data may be used to create a TTI curve which shows peaks which each represent a chest compression.

In determining a timing for a mechanical ventilator, the method may comprise determining the number of chest compressions since the last ventilation was provided (or since the counting was started if no ventilations have previously been provided). The determined timing for a mechanical ventilator to provide a ventilation (or two or more ventilations) may be after a given number of chest compressions has been performed since the last ventilation. For example, after a predetermined number of compressions, which may be any number between 3 and 15, or 5 and 12 such as 5, 6, 7, 8, 9, 10, 11, or 12. Alternatively, the predetermined number of chest compressions before a ventilation is performed may be 30, for example it may be between 10 and 50, 20 and 40 or 25 and 35.

For example, every set number of chest compressions, such as every tenth chest compression, a signal may be sent to the mechanical ventilator to cause it to provide a ventilation (or two or more ventilations). The signal may cause the ventilation(s) to be provided between two of the chest compressions. For example, the first ventilation may be provided after the tenth chest compression but before (the entire tidal volume having been administered before the next chest compression starts) the eleventh chest compression, the next ventilation may be provided after the twentieth chest compression but before the twenty first chest compression and so on.

Once the predetermined number of chest compressions has been performed (as determined from the TTI measurement) the method may comprise sending a signal to the mechanical ventilator to provide at least one ventilation. The predetermined number of chest compressions between ventilations (i.e. the number of chest compression before a trigger signal is sent) may be set (and/or adjusted) before and/or during CPR. As mentioned above, this may be so as to cause a certain ratio of chest compressions: ventilations.

Once a signal is received by a mechanical ventilator to provide a ventilation, a stored tidal volume of air may be provided to the patient. The tidal volume may be based on one or more patient characteristics such as height, weight, age and sex. The method may comprise determining a tidal volume for the ventilations based on one or more patient characteristics. The method may comprise inputting one or more patient characteristics so that the ventilator or a separate controller can determine the tidal volume.

The determined timing for a mechanical ventilator to provide a ventilation (or two or more ventilations) may be a time between two chest compressions, such as immediately after one of the chest compressions has been performed. This means that is it possible to prevent a ventilation being provided when a chest compression is being performed. The signal may cause the mechanical ventilator to provide the ventilation(s) to the patient between two chest compressions.

The determined timing for a mechanical ventilator to provide a ventilation may be immediately (e.g. within 100, 75, 50, 25, 10, or 5 ms) after a chest compression is performed.

The signal may cause the mechanical ventilator to immediately (e.g. within 100, 75, 50, 25, 10, 5 ms) provide the ventilation after the last chest compression.

In a preferred embodiment, the ventilation is entirely provided before the next compression starts.

The signal sent to the ventilator may comprise an indication of a time over which the ventilation is to be provided. The time between compressions (which may be the average time between the compressions since the last ventilation was provided) may be determined and the time over which the ventilation(s) is provided may be based on the length of time between compressions. Preferably each ventilation is entirely provided within 200, 150, 100, 50, 25, 10, 5, 4, 3, or 2 ms. This means that the ventilation(s) can be provided before the next chest compression starts which can reduce the risk of intrathoracic damage. Additionally, by providing the ventilation(s) in a quick, sharp burst, a better ventilation can be administered. This type of quick ventilation is difficult to achieve with manual ventilations.

The ventilator may charge (i.e. fill up) with a determined tidal volume before a signal is sent to administer the ventilation. For example, the ventilator may charge immediately after a ventilation is released. This means that it is possible to provide the quick ventilation described above.

In a second aspect the present invention provides a computer program product comprising instructions that when executed on a controller will configure the controller to be arranged to receive a measurement of transthoracic impedance of a patient obtained during chest compressions; determine a timing for a mechanical ventilator to provide a ventilation based on the measurement of transthoracic impedance; and provide a signal to control a mechanical ventilator based on the determined timing.

The computer program product of the second aspect may also configure the controller to perform one or more of the additional features described above in relation to the method of the first aspect.

In a third aspect the present invention provides a controller for controlling a mechanical ventilator, the controller being arranged to receive a measurement of transthoracic impedance of a patient which has been obtained during chest compressions; determine a timing for a mechanical ventilator to provide a ventilation based on the measurement of transthoracic impedance; and send a signal to control the mechanical ventilator based on the determined timing.

Thus the present invention may provide a controller for controlling a mechanical ventilator so that it provides a ventilation at the correct time during CPR. This is achieved by monitoring the transthoracic impedance (TTI) of the patient during chest compressions and controlling the mechanical ventilator based on this monitored parameter. This means that ventilation during chest compressions can be provided reliably and at the correct time relative to the chest compressions.

The controller may be arranged to control the mechanical ventilator to provide a ventilation between two chest compressions. This may be achieved by sending a signal which causes the ventilation to be performed immediately after one of the chest compressions is performed and by providing the ventilation over a time period which is less than the average time between two chest compressions.

The transthoracic impedance measurements may be used to determine a timing for a mechanical ventilator to be triggered. Thus, the signal to control the mechanical ventilator may be a trigger signal. The trigger signal may be arranged to cause one or more, such as two, ventilations to be administered.

The determined timing may be so as to provide a certain (e.g. predetermined) ratio of compressions to ventilations. This may be when the patient being ventilated has an unsecured airway.

The determined timing may therefore be so as to cause a ventilation to be provided between two chest compressions and/or so as to cause a certain ratio of chest compressions: ventilations.

The controller may be arranged to receive a ratio of compressions to ventilations which controls the ratio of compressions to ventilations.

The ratio of compressions to ventilations may be set according to medical guidelines. As a result, the ratio of compressions to ventilations may change over time and may be different between infants, children and adults.

Currently the recommended ratio for adults is 30:2 and hence the determined timing may be such as to cause the ratio of chest compressions to ventilations to be 30:2. However the recommended ratio has been known to be 15:2. Therefore the guidelines can change and thus the desired ratio of chest compressions to ventilations may vary over the years. Thus the determined timing may be so as to cause the ratio of chest compressions: ventilations to be according to current medical guidelines.

The ratio of chest compressions: ventilations may be 30:2 or 15:2 or between 15:2 and 30:2, such as 10:1. The ratio may depend on the recommended medical guidelines at the time the method is performed.

When the patient has an unsecured airway it may be necessary for chest compressions to be paused whilst the ventilation is provided. This is to minimise the risk that a ventilation is provided whilst a chest compression is performed.

If there is a pause, it is preferable for the pause to not be more than one or two seconds during continuous chest compressions, in accordance with the Guidelines for the compression: ventilation ratios.

Thus, the controller may be arranged to cause an indication signal indicating that the chest compressions should be paused so a ventilation can be provided safely. For example, the indication signal could be caused after a certain number (such as 15, 5, 4 or 3) of chest compressions has been performed.

The indication signal may be an audible signal such as a beep, and/or a visual signal, such as a light flash.

The controller may be part of the mechanical ventilator or it may be provided separately.

The controller may be arranged to determine the number of chest compressions since the last ventilation was provided (or since the counting was started if no ventilations have previously been provided). The determined timing for a mechanical ventilator to provide a ventilation (or two or more ventilations) may be after a given number of chest compressions has been identified as having been performed since the last ventilation. For example, after a predetermined number of compressions, which may be any number between 3 and 15, or 5 and 12 such as 5, 6, 7, 8, 9, 10, 11 or 12, the controller may be arranged to produce the signal for the mechanical ventilator. The predetermined number of chest compressions before a ventilation is performed may alternatively be 30, for example it may be between 10 and 50, 20 and 40 or 25 and 35.

Once a predetermined number of chest compressions has been performed (as determined from the TTI measurement) the controller may be arranged to send a signal to the mechanical ventilator to provide at least one ventilation. The signal may cause the ventilator to provide a ventilation when the chest is not being compressed, i.e. between two chest compressions. The predetermined number of chest compressions between ventilations may be input to the controller (and/or adjusted) before and/or during CPR. This may control the ratio of chest compressions: ventilations.

The controller may be arranged to determine a tidal volume that the mechanical ventilator should administer. The determined tidal volume may be based on one or more patient characteristics such as height, weight, age and sex. The controller may be arranged to receive an input of one or more patient characteristics and then determine the tidal volume based, at least in part, on the input.

The controller may be arranged to also provide a signal that includes an indication of the time over which the ventilation is to be provided. The time between chest compressions may be determined and the time over which the ventilation is provided may be based on the length of time between compressions. In an embodiment the signal comprises an instruction that the ventilation(s) (a full tidal volume) is entirely provided within 200, 150, 100, 50, 25, 10, 5, 4, 3, or 2 ms. This means that the ventilation(s) can be provided before the next chest compression starts which can reduce the risk of intrathoracic damage. Additionally, by providing the ventilation in a quick, sharp burst, a more appropriate ventilation can be administered. This type of quick ventilation is difficult to achieve with manual ventilations.

In a fourth aspect the present invention provides an apparatus for providing a mechanical ventilation to a patient during chest compressions, the apparatus comprising: a transthoracic impedance measurement device for measuring the transthoracic impedance of a patient during chest compressions; a controller arranged to receive the measurement of transthoracic impedance of a patient during chest compressions from the measurement device, determine a timing for a mechanical ventilator to provide a ventilation based on the measurement and produce a signal based on the determined timing; and a mechanical ventilator arranged to provide a mechanical ventilation based on the signal received from the controller.

In other words, the present invention also provides an apparatus which comprises the controller of the third aspect in addition to a transthoracic impedance measurement device and a mechanical ventilator. The TTI measurement device provides the input to the controller, and the mechanical ventilator receives the output from the controller.

The ventilator may be arranged to only provide a ventilation when a signal is received from the controller to perform a ventilation. In other words, the method may be such that each time it is desired to provide a ventilation to the patient, a signal is sent from the controller to the ventilator.

The ventilator may not provide ventilations at a certain or predetermined rate. Instead the ventilator may provide ventilations only when a signal is received from the controller. The timing of the signals may be dependent on the time over which a number of chest compressions is performed.

When the patient has an unsecured airway it may be necessary for chest compressions to be paused whilst the ventilation is provided. This is to minimise the risk that a ventilation is provided whilst a chest compression is performed.

If there is a pause, it is preferable for the pause to not be more than one or two seconds during continuous chest compressions, in accordance with the Guidelines for the compression: ventilation ratios.

Thus, the apparatus may have an indication signal output device which is for providing an indication signal indicating that the chest compressions should be paused so a ventilation can be provided safely. For example, the indication signal output device could be activated after a certain number (such as 15, 5, 4 or 3) of chest compressions has been performed.

The indication signal may be an audible signal such as a beep, and/or a visual signal, such as a light flash.

The TTI measurement device may comprise at least two electrodes. In an embodiment the TTI measurement device comprises four electrodes so as to avoid introducing the electrodes' impedance in the measurement. When there are four electrodes, two electrodes may be used for applying a current to the thoracic cavity and two may be for picking up a voltage signal. It is possible to position one current electrode and one voltage electrode in the same pad so that only two pads are placed on the patient's thorax.

In an embodiment the current used by the TTI measurement device is an alternating current with a frequency range of between 50 and 100 kHz, e.g. 80 kHz.

The TTI measurement device may be part of the mechanical ventilator, or provided as a separate device. The TTI measurement device may be part of a defibrillator.

In a fifth aspect the present invention provides a method of ventilating a patient during chest compressions, the method comprising: performing chest compressions; measuring transthoracic impedance of the patient during the chest compressions; determining a timing for a mechanical ventilator to provide a ventilation based on the measurement of transthoracic impedance; and ventilating a patient using a mechanical ventilator, wherein ventilations are provided based on the determined timing.

The method may comprise controlling the mechanical or automatic ventilator to provide a ventilation at the correct time during CPR. This may be achieved by monitoring the transthoracic impedance (TTI) of the patient during chest compressions and controlling the mechanical ventilator based on this monitored parameter. This means that ventilation during chest compressions can be provided reliably and at the correct time relative to the chest compressions.

The method may control the mechanical ventilator to provide a ventilation between two chest compressions. This may be achieved by causing the ventilation to be performed immediately after one of the chest compressions is performed and by providing the ventilation over a time period which is equal to, or less than, the average time between two chest compressions.

As a result, transthoracic impedance fluctuations generated by chest compressions may be used to synchronize ventilations between two chest compressions.

The transthoracic impedance measurements may be used to determine timing for a mechanical ventilator to be triggered. Thus, a signal to control the mechanical ventilator may be a trigger signal.

The determined timing may be so as to provide a certain (e.g. predetermined) ratio of chest compressions to ventilations. This may be when the patient being ventilated has an unsecured airway.

The determined timing may therefore be so as to cause a ventilation to be provided between two chest compressions and/or so as to cause a certain ratio of chest compressions: ventilations.

The method may include inputting or setting a ratio of compressions to ventilations which controls the ratio of compressions to ventilations.

The ratio of compressions to ventilations may be set according to medical guidelines. As a result, the ratio of compressions to ventilations may change over time and may be different between infants, children and adults.

Currently the recommended ratio for adults is 30:2 and hence the determined timing may be such as to cause the ratio of chest compressions to ventilations to be 30:2. However the recommended ratio has been known to be 15:2. In other words the guidelines can change and thus the desired ratio of chest compressions to ventilations may vary over the years. Thus the determined timing may be so as to cause the ratio of chest compressions: ventilations to be according to current medical guidelines.

The ratio of chest compressions: ventilations may be 30:2 or 10:1 or 15:2, or between 15:2 and 30:2, and this may depend on the recommended medical guidelines at the time the method is performed.

For example, when the ratio of chest compressions to ventilations is 30:2, 30 chest compressions may be performed and then two ventilations may be provided before the next chest compression is performed.

When the patient has an unsecured airway it may be necessary for chest compressions to be paused whilst the ventilation is provided. This is to minimise the risk that a ventilation is provided whilst a chest compression is performed.

If there is a pause, it is preferable for the pause to not be more than one or two seconds during continuous chest compressions, in accordance with the Guidelines for the compression: ventilation ratios.

Thus, an indication signal may be provided indicating that the chest compressions should be paused so a ventilation can be provided safely. For example, the indication signal could be activated after a certain number (such as 15, 5, 4 or 3) of chest compressions has been performed.

The indication signal may be an audible signal such as a beep, and/or a visual signal, such as a light flash.

The chest compressions may be being performed manually or performed by a machine.

The transthoracic impedance may be measured using a TTI measurement device. The TTI measurement device may comprise at least two electrodes. To obtain a TTI measurement, the electrodes may be placed on a patient's thorax, and then a current sent through the electrodes. The voltage drop across the electrodes may then be monitored to obtain an impedance value which is a transthoracic impedance value.

This data may be used to create a TTI curve which shows peaks which each represent a chest compression.

In determining a timing for a mechanical ventilator, the method may comprise determining the number of chest compressions since the last ventilation was provided (or since the counting was started if no ventilations have previously been provided). The determined timing for a mechanical ventilator to provide a ventilation may be after a given number of chest compressions has been performed since the last ventilation. For example, after a predetermined number of compressions, which may be any number between 3 and 15, or 5 and 12 such as 5, 6, 7, 8, 9, 10, 11, or 12. Alternatively, the predetermined number of chest compressions before a ventilation is performed may be 30, for example it may be between 10 and 50, 20 and 40 or 25 and 35.

For example, every set number of chest compressions, such as every tenth chest compression, a signal may be sent to the mechanical ventilator to cause it to provide a ventilation. The signal may cause the ventilation to be provided between two of the chest compressions. For example, the first ventilation may be provided after the tenth chest compression but before (the entire tidal volume having been administered before the next chest compression starts) the eleventh chest compression, the next ventilation may be provided after the twentieth chest compression but before the twenty first chest compression and so on.

Once the predetermined number of chest compressions has been performed (as determined from the TTI measurement) the method may comprise sending a signal to the mechanical ventilator to provide a ventilation. The predetermined number of chest compressions between ventilations may be set (and/or adjusted) before and/or during CPR. This may set a ratio of chest compressions: ventilations.

Once a signal is received by a mechanical ventilator to provide a ventilation, a stored tidal volume of air may be provided to the patient. The tidal volume may be based on one or more patient characteristics such as height, weight, age and sex.

The method may comprise determining a tidal volume for the ventilations based on one or more patient characteristics.

The method may comprise inputting one or more patient characteristics so that the ventilator or a separate controller can determine the tidal volume.

The determined timing over which the mechanical ventilator provides a ventilation may be equal to or less than the time between two chest compressions. This means that is it possible to prevent a ventilation being provided when a chest compression is being performed. The signal may cause the mechanical ventilator to provide the ventilation to the patient between two chest compressions and to have finished providing the ventilation before the next chest compression starts.

The determined timing for a mechanical ventilator to provide a ventilation may be immediately (e.g. within 100, 75, 50, 25, 10, or 5 ms) after a chest compression is performed.

The mechanical ventilator may immediately (e.g. within 100, 75, 50, 25, 10, or 5 ms) provide the ventilation after the last chest compression. In a preferred embodiment, the ventilation is entirely provided before the next compression starts.

The ventilator may be controlled to control the time over which the ventilation is to be provided. The time between compressions (which may be the average time between the compressions since the last ventilation was provided) may be determined and the time over which the ventilation is provided may be based on the length of time between compressions. Preferably the ventilation is entirely provided within 200, 150, 100, 50, 25, 10, 5, 4, 3, or 2 ms. This means that the ventilation can be provided before the next chest compression starts which can reduce the risk of intrathoracic damage. Additionally, by providing the ventilation in a quick, sharp burst, a better ventilation can be administered. This type of quick ventilation is difficult to achieve with manual ventilations.

The ventilator may charge (i.e. fill up) with a determined tidal volume before a trigger signal is sent to administer the ventilation. For example, the ventilator may charge immediately after a ventilation is released. This means that it is possible to provide the quick ventilation described above.

Any features or optional features of any one of the aspects of the invention are applicable to each of the other aspects of the invention.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

Certain preferred embodiments of the present invention will now be described by way of example only with reference to the accompanying drawings, in which.

DETAILED DESCRIPTION

Figure 1:
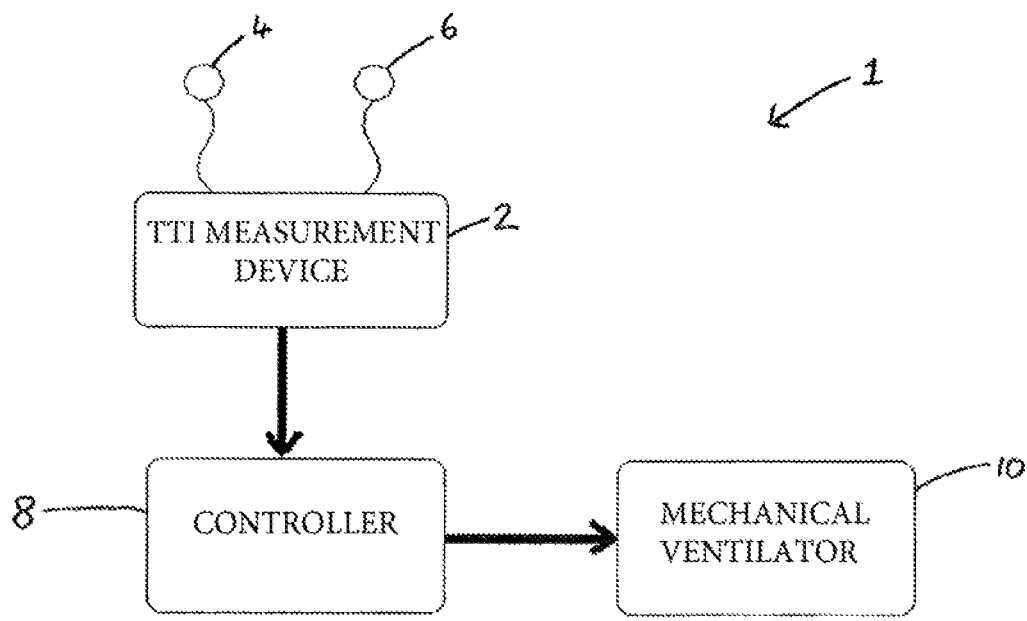
FIG. 1 is a schematic diagram of an apparatus for providing a mechanical ventilation to a patient during chest compressions.

FIG. 1 shows an apparatus 1 for providing a mechanical ventilation to a patient during chest compressions. The apparatus 1 comprises a transthoracic impedance (TTI) measurement device 2. The measurement device 2 comprises two electrodes 4, 6.

The measurement device 2 provides an input for a controller 8 which provides a control signal for a mechanical ventilator 10.

The TTI measurement device 2 is used to obtain a measurement of the transthoracic impedance of a patient during chest compressions.

Figure 2:
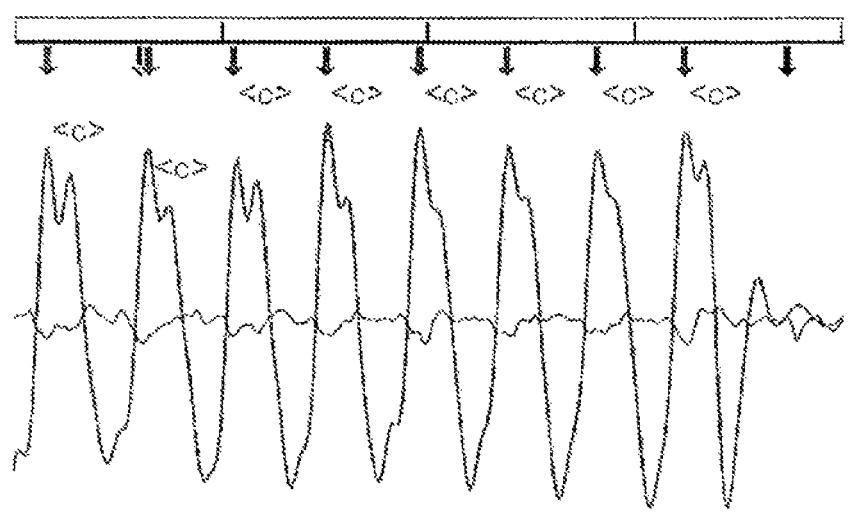
FIG. 2 shows a transthoracic impedance curve during chest compressions.

The electrodes 4, 6 are placed in contact with the patient's thorax and a current is applied to the electrodes 4,6. This produces a voltage drop signal which depends on the impedance of the thorax. This resulting signal during chest compressions is shown in FIG. 2 in the form of a transthoracic impedance curve. This signal is sent to the controller 8.

The transthoracic impedance of inflated lungs is different from the impedance of deflated (or empty) lungs. Therefore, as chest compression are performed the measured impedance changes as shown in FIG. 2. Each peak represents a chest compression.

The controller 8 counts the number of chest compressions. After a given number of chest compressions have been identified, for example after 10 chest compressions, a signal is sent to the mechanical ventilator 10 to provide a ventilation or two ventilations. The signal is such that the ventilation(s) is performed between two chest compressions. This may be achieved by causing a ventilation to be performed immediately after one of the chest compressions is performed and over a time period which is less than the average time between two chest compressions.

The signal may also cause the ratio of chest compressions: ventilations to be according to current medical guidelines, for example 30:2.

The mechanical ventilator 10 provides a set tidal volume to the patient immediately (within 10 ms) after the 10th chest compression. The ventilation is provided in less than 50 ms.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

What is claimed is:

1. A non-transitory computer readable medium comprising instructions that when executed on a controller will configure the controller to be arranged to perform a method, the method comprising:
    receiving a measurement of transthoracic impedance of a patient obtained during chest compressions, wherein the measurement of transthoracic impedance comprises measuring fluctuations in transthoracic impedance in the thoracic cavity generated by chest compressions to determine when the chest compressions are performed;
    determining a first time period between the chest compressions based on the measurement of transthoracic impedance;
    determining a timing for a mechanical ventilator to perform a ventilation between chest compressions for a second time period that is less than the first time period;
    sending a signal to control the mechanical ventilator based on the determined timing; and
    providing a mechanical ventilation based on the signal.

2. The non-transitory computer readable medium as claimed in claim 1, wherein the signal is a trigger signal which causes the mechanical ventilator to provide the ventilation.

3. The non-transitory computer readable medium as claimed in claim 1, wherein the steps of determining the timing for a mechanical ventilator and sending the signal to the mechanical ventilator comprise:
    determining the number of chest compressions since the last ventilation was provided; and
    sending the signal after a predetermined number of chest compressions has been performed.

4. The non-transitory computer readable medium as claimed in claim 3, wherein the predetermined number of chest compressions is between 25 and 35.

5. The non-transitory computer readable medium as claimed in claim 1, wherein the mechanical ventilation is provided within 10 ms of a last chest compression.

6. The non-transitory computer readable medium as claimed in claim 1, wherein the mechanical ventilation provides a set tidal volume in each ventilation.

7. The non-transitory computer readable medium as claimed in claim 6, wherein the tidal volume is provided to the patient within 100 ms.

8. A controller for controlling a mechanical ventilator, the controller being arranged to:
    receive a measurement of transthoracic impedance of a patient which has been obtained during chest compressions, wherein the measurement of transthoracic impedance comprises measuring fluctuations in transthoracic impedance in the thoracic cavity generated by chest compressions to determine when the chest compressions are performed;
    determine a first time period between the chest compressions based on the measurement of transthoracic impedance;
    determine a timing for a mechanical ventilator to perform a ventilation between chest compressions for a second time period that is less than the first time period; and
    send a signal to control the mechanical ventilator based on the determined timing.

9. The controller as claimed in claim 8, wherein the signal is a trigger signal which causes the mechanical ventilator to provide the ventilation.

10. The controller as claimed in claim 8, wherein the controller is arranged to determine the number of chest compressions since the last ventilation was provided;
    and send the signal after a predetermined number of chest compressions has been performed.

11. The controller as claimed in claim 10, wherein the predetermined number of chest compressions is between 5 and 12.

12. An apparatus for providing a mechanical ventilation to a patient during chest compressions, the apparatus comprising:
    a transthoracic impedance measurement device for measuring the transthoracic impedance of a patient during chest compressions;
    a controller as claimed in claim 8; and
    a mechanical ventilator arranged to provide a mechanical ventilation based on the signal received from the controller.

13. The apparatus as claimed in claim 12, wherein the apparatus is arranged so that the mechanical ventilation is provided within 10 ms of a last chest compression.

14. The apparatus as claimed in claim 12, wherein the mechanical ventilator is arranged to provide a set tidal volume in each ventilation.

15. The apparatus as claimed in claim 14, wherein the ventilator is arranged to provide the tidal volume to the patient within 100 ms.

16. A method of ventilating a patient during chest compressions, the method comprising:
    performing chest compressions;
    measuring transthoracic impedance of the patient during the chest compressions, wherein the measurement of transthoracic impedance comprises measuring fluctuations in transthoracic impedance in the thoracic cavity generated by chest compressions to determine when the chest compressions are formed;
    determining a first time period between the chest compressions based on the measurement of transthoracic impedance;
    determining a timing for a mechanical ventilator to perform a ventilation between chest compressions for a second time period that is less than the first time period; and
    ventilating the patient using the mechanical ventilator, wherein ventilations are provided based on the determined timing.

17. The method as claimed in claim 16, wherein the steps of determining the timing for a mechanical ventilator, and ventilating the patient comprise:
    determining the number of chest compressions since the last ventilation was provided; and providing the ventilation to the patient after a predetermined number of chest compressions has been performed.

18. The method as claimed in claim 17, wherein the predetermined number of chest compressions is between 25 and 35.

19. The method as claimed in claim 16, wherein each ventilation is provided within 10 ms of a last chest compression.

20. The method as claimed in claim 16, wherein the ventilator provides a set tidal volume in each ventilation.

21. The method as claimed in claim 20, wherein the tidal volume is provided to the patient within 100 ms.

* * * * *